(12) United States Patent
He et al.

(10) Patent No.: US 9,612,207 B2
(45) Date of Patent: Apr. 4, 2017

(54) SMART WINDOW FOR SEMICONDUCTOR PROCESSING TOOL

(71) Applicant: Lam Research Corporation, Fremont, CA (US)

(72) Inventors: Xinxin He, Vancouver, WA (US); Cameron Paul Simoes, Tualatin, OR (US)

(73) Assignee: Lam Research Corporation, Fremont, CA (US)

( * ) Notice: Subject to any disclaimer, the term of this patent is extended or adjusted under 35 U.S.C. 154(b) by 0 days.

(21) Appl. No.: 14/795,785

(22) Filed: Jul. 9, 2015

(65) Prior Publication Data

US 2017/0010218 A1  Jan. 12, 2017

(51) Int. Cl.
*G02F 1/15* (2006.01)
*G02B 26/00* (2006.01)
*G01N 21/88* (2006.01)
*G02F 1/17* (2006.01)
*G02F 1/01* (2006.01)
*G01N 21/95* (2006.01)

(52) U.S. Cl.
CPC ..... *G01N 21/8806* (2013.01); *G01N 21/9501* (2013.01); *G02F 1/0102* (2013.01); *G02F 1/0121* (2013.01); *G02F 1/172* (2013.01)

(58) Field of Classification Search
CPC  G02B 26/00; G02B 26/02; G02F 1/00; G02F 1/01; G02F 1/0018; G02F 1/07; G02F 1/03; G02F 1/167
USPC ................ 359/237, 238, 245, 265, 296, 315
See application file for complete search history.

(56) References Cited

U.S. PATENT DOCUMENTS

| 6,429,961 B1 * | 8/2002 | Harary ............. B32B 17/10055 359/265 |
| 2014/0118810 A1 | 5/2014 | Mohat |
| 2014/0177025 A1 | 6/2014 | Lee et al. |

OTHER PUBLICATIONS

SONTE LLC, "SONTE Hub Wi-Fi Control for SONTE Film" User Guide, created on May 9, 2014 based upon "Created" date in "Document Properties" of downloaded .pdf file, http://sonte.com/wp-content/uploads/2012/12/SONTE-Hub-Guidel.pdf.

(Continued)

*Primary Examiner* — William Choi
(74) *Attorney, Agent, or Firm* — Weaver Austin Villeneuve & Sampson LLP

(57) ABSTRACT

Semiconductor processing tool smart window kits, and smart windows for semiconductor processing tools and semiconductor processing tool doors, are discussed herein. Some smart windows may include a smart film with an active area that is electronically controllable between an opaque state and a transparent state, and that may be configured to prevent light from passing through the smart window and entering into a semiconductor processing tool and/or semiconductor processing chamber when in the opaque state. Additional components, configurations, and/or systems of some kits and smart windows are further discussed herein, which may include an electrical contact cover that may be configured to electrically connect the smart film to a power source and a smart film controller that may be configured to cause a smart film to transition between the opaque and transparent states.

27 Claims, 9 Drawing Sheets

(56) References Cited

OTHER PUBLICATIONS

SONTE LLC, "Instruction Manual: SONTE RF: RF Control for SONTE Film," created on Oct. 30, 2014 based upon "Created" date in "Document Properties" of downloaded .pdf file, http://sonte.com/wp-content/uploads/2012/12/RF-Manual.pdf.
SONTE LLC, "Tomorrow. Today," Specification, created on Feb. 17, 2014 based upon "Created" date in "Document Properties" of downloaded .pdf file, http://sonte.com/wp-content/uploads/2012/12/SONTE-Film-Specification%EF%BC%88V3.0.pdf.
SONTE LLC, "Instruction Manual: SONTE Film Installation Guide," created on Dec. 24, 2014 based upon "Created" date in "Document Properties" of downloaded .pdf file, http://sonte.com/wp-content/uploads/2012/12/SONTE-Film-Installation-Guide-Dec-2014.pdf.
SONTE LLC, "Brochure" SONTE Brochure created on Feb. 17, 2014 based upon "Created" date in "Document Properties" of downloaded .pdf file, http://sonte.com/wp-content/uploads/2012/12/ssb2014v7OL2p1.pdf.
SONTE LLC, "SONTE Installation Tools Guide," User Guide, created on May 13, 2014 based upon "Created" date in "Document Properties" of downloaded .pdf file, http://sonte.com/wp-content/uploads/2012/12/Installation-Tools-Guide1.pdf.
Smart Tint, Inc., "Specifications: Smart Tint $6^{th}$ Generation SmartCling," Specification, publication date unable to be determined, downloaded in Jul. 2015, http://www.smarttint.com/specs/SmartTint-SmartCling.pdf.
Smart Tint, Inc., "Smart Tint Technical Data Sheet," Data Sheet, unknown creation or publication date unable to be determined, downloaded in Jul. 2015, http://www.smarttint.com/specs/specsheet-smart-tint.pdf.
SONTE LLC, "SONTE Hub Wi-Fi Control for SONTE Film," User Guide, http://sonte.com/downloads.
SONTE LLC, "SONTE RF: RF Control for SONTE Film," Instruction Manual, http://sonte.com/downloads.
SONTE LLC, "Tomorrow . Today," Specification, http://sonte.com/downloads.
SONTE LLC, "SONTE Film Installation Guide," Instruction Manual, Dec. 2014, http://sonte.com/downloads.
SONTE LLC, "SONTE," Brochure, http://sonte.com/downloads.
SONTE LLC, "SONTE Installation Tools Guide," User Guide, 2014, http://sonte.com/downloads.
Smart Tint, Inc., "Specifications: Smart Tint $6^{th}$ Generation SmartCling," Specification, http://www.smarttint.com.
Smart Tint, Inc., "Smart Tint Technical Data Sheet," Data Sheet, http://www.smarttint.com.

\* cited by examiner

SMART WINDOW FOR SEMICONDUCTOR PROCESSING TOOL

BACKGROUND

Semiconductor processing tools often include inspection windows which allow for viewing the inside of the semiconductor processing tool, including into the semiconductor processing chamber. These windows are typically set into a door panel or wall panel of the semiconductor processing tool and generally do not have a cover, which may permit light to enter into the semiconductor processing tool and contact a semiconductor wafer.

BRIEF DESCRIPTION OF THE DRAWINGS

FIGS. 1, 3 through 5, 8, and 9 are to-scale within each Figure, although not necessarily from Figure to Figure.

SUMMARY

Figure 1:
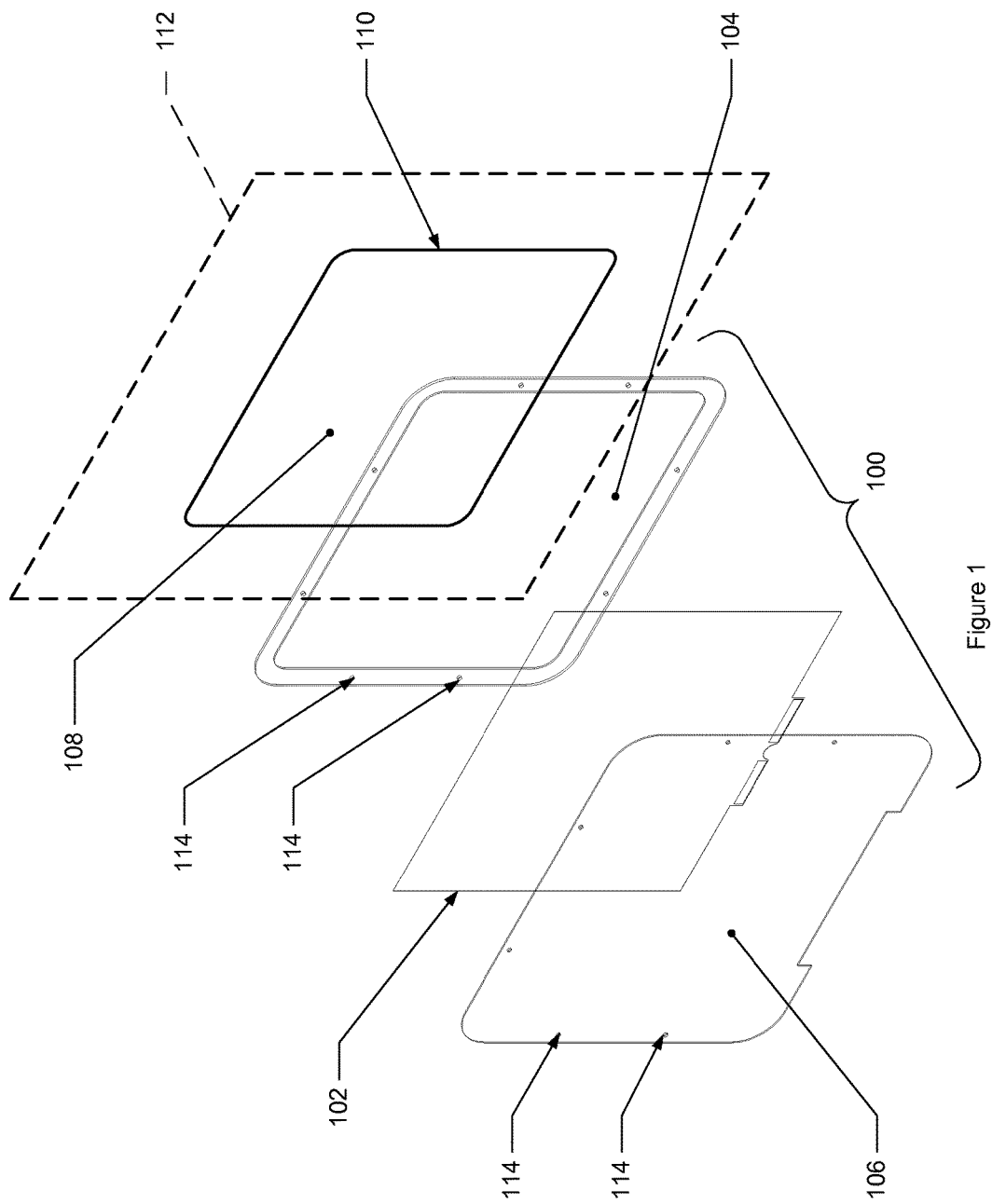
FIG. 1 depicts an isometric exploded view of a first example semiconductor processing tool smart window kit for a semiconductor processing tool.

The systems, methods and devices of this disclosure each have several innovative aspects, no single one of which is solely responsible for the desirable attributes disclosed herein. Included among these aspects are at least the following implementations, although further implementations may be set forth in the detailed description or may be evident from the discussion provided herein.

In one embodiment, a semiconductor processing tool smart window kit for a semiconductor processing tool including at least one first inspection window set in a first opening defined by a first boundary may be provided. The semiconductor processing tool smart window kit may also include a smart film that has an active area that is electronically controllable between a transparent state and an opaque state. Such an active area may be defined by a second boundary that may be sized larger than the first boundary. The smart film may be configured to be installed adjacent to the first inspection window.

In one such embodiment, the semiconductor processing tool smart window kit may also include the first inspection window and the smart film may have an adhesive backing configured to allow the smart film to be adhered to the first inspection window.

In further such embodiments, the semiconductor processing tool smart window kit may further include a first panel that is transparent. The smart film may also be configured to be interposed between the first inspection window and the first panel, and the smart film may be configured to be adhered to an item such as the first panel or the first inspection window.

In one such embodiment, the semiconductor processing tool smart window kit may also include an electrical contact cover, as well as a first electrical conductor, a second electrical conductor, and a connector. The smart film may also include a first electrical contact pad and a second electrical contact pad. The first electrical conductor may be electrically connected to the first electrical contact pad, the second electrical conductor may be electrically connected to the second electrical contact pad, and the first electrical conductor and the second electrical conductor may be connected with the connector.

In further such embodiments, the semiconductor processing tool smart window kit's electrical contact cover may be configured to be affixed to the first inspection window so as to cover the electrical contact pads.

In some further embodiments, the electrical contact cover may also be configured to be affixed to an item such as the first inspection window or the first panel.

In some embodiments, the semiconductor processing tool smart window kit may also include a smart film controller. The smart film controller may include a transformer, at least one circuit breaker, and at least one smart film control switch. The at least one circuit breaker and the transformer may be configured to be electrically connected to a power source, the at least one circuit breaker and the transformer may be electrically connected to the at least one smart film control switch, the at least one smart film control switch may be electrically connected to at least one smart film, and the at least one smart film control switch may be configured to cause the at least one smart film to transition between the transparent state and the opaque state when actuated when the at least one circuit breaker and the transformer are electrically connected to the power source.

In one embodiment, a door for a semiconductor processing tool may be provided. The door may include a door panel, mechanical features to operably connect the door panel to the semiconductor processing tool, a first inspection window set in a first opening in the door panel, and a smart film that may have an active area that is electronically controllable between a transparent state and an opaque state. Such an active area may be defined by a second boundary that may be sized larger than the first boundary.

In some embodiments, the door's smart film may be adhered to the first inspection window with an adhesive layer.

In some embodiments, the door may also include a first panel that is transparent. The smart film may also be interposed between the first inspection window and the first panel, and the smart film may be adhered to an item such as the first panel or the first inspection window.

In one such embodiment, the door may also include an electrical contact cover. The electrical contact cover may include a first electrical conductor, a second electrical conductor, and a connector. The smart film may also include a first electrical contact pad and a second electrical contact pad. The first electrical conductor may be electrically connected to the first electrical contact pad, the second electrical conductor may be electrically connected to the second electrical contact pad, and the first electrical conductor and the second electrical conductor may be connected with the connector.

In further such embodiments, the door's electrical contact may be configured to be affixed to the first inspection window.

In further such embodiments, the door may further include a first panel that is transparent. The smart film may be interposed between the first inspection window and the first panel, and the smart film may be adhered to an item such as the first panel or the first inspection window. The electrical contact cover may also be configured to be affixed to an item such as the first inspection window or the first panel.

In some embodiments, the door may also include a smart film controller. The smart film controller may include a transformer, at least one circuit breaker, and at least one smart film control switch. The at least one circuit breaker and the transformer may be configured to be electrically connected to a power source, the at least one circuit breaker and the transformer may be electrically connected to the at least one smart film control switch, the at least one smart film control switch may be electrically connected to at least one smart film, and the at least one smart film control switch may be configured to cause the at least one smart film to transition between the transparent state and the opaque state when actuated and when the at least one circuit breaker and the transformer are electrically connected to the power source.

In one embodiment, a semiconductor processing tool may be provided. The semiconductor processing tool may include a first inspection window set in a first opening in the semiconductor processing tool, and a smart film that may have an active area that is electronically controllable between a transparent state and an opaque state. The first opening may be defined by a first boundary and the active area may be defined by a second boundary that may be sized larger than the first boundary. The smart film may be configured to be installed adjacent to the first inspection window. In some such embodiments, the semiconductor processing tool's smart film may be adhered to the first inspection window with an adhesive layer.

In some embodiments, the semiconductor processing tool may also include a first panel that is transparent. The smart film may also be interposed between the first inspection window and the first panel, and the smart film may be adhered to an item such as the first panel or the first inspection window.

In some such embodiments, the semiconductor processing tool may also include an electrical contact cover. The electrical contact cover may include a first electrical conductor, a second electrical conductor, and a connector. The smart film may also include a first electrical contact pad and a second electrical contact pad. The first electrical conductor may be electrically connected to the first electrical contact pad, the second electrical conductor may be electrically connected to the second electrical contact pad, and the first electrical conductor and the second electrical conductor may be connected with the connector.

In further such embodiments, the electrical contact cover may be configured to be affixed to the first inspection window.

In further such embodiments, the semiconductor processing tool may further include a first panel that is transparent. The smart film may be interposed between the first inspection window and the first panel, and the smart film may be adhered to an item such as the first panel or the first inspection window. The electrical contact cover may also be configured to be affixed to an item such as the first inspection window or the first panel.

In some embodiments, the semiconductor processing tool may also include a smart film controller. The smart film controller may include a transformer, at least one circuit breaker, and at least one smart film control switch. The at least one circuit breaker and the transformer may be configured to be electrically connected to a power source, the at least one circuit breaker and the transformer may be electrically connected to the at least one smart film control switch, the at least one smart film control switch may be electrically connected to at least one smart film, and the at least one smart film control switch may be configured to cause the at least one smart film to transition between the transparent state and the opaque state when actuated and when the at least one circuit breaker and the transformer are electrically connected to the power source.

In some embodiments, the semiconductor processing tool may also include a semiconductor processing controller that may have at least one memory and at least one processor communicatively connected with the memory and that may be configured to be communicatively connected with the smart film and the semiconductor processing tool. The at least one memory may stores computer-executable instructions for controlling the at least one processor to receive a signal from the semiconductor processing tool that indicates that the semiconductor processing tool is engaged in performing a first semiconductor manufacturing process on a semiconductor wafer and cause, in response to receiving the signal and when the smart film is in the transparent state, the smart film to enter the opaque state.

In some embodiments, the semiconductor processing tool may also include a switch and a lockout. The switch may be electrically connected to the smart film and may be configured to cause the smart film to transition between the transparent state and the opaque state. The lockout may also be configured to prevent the switch from causing the smart film to transition into the transparent state during a phase of semiconductor processing when the smart film is associated with being in an opaque state.

Details of one or more implementations of the subject matter described in this disclosure are set forth in the accompanying drawings and the description below. Other features, aspects, and advantages will become apparent from the description, the drawings and the claims. Note that the relative dimensions of the following figures may not be drawn to scale, unless otherwise indicated.

DETAILED DESCRIPTION

In the following description, numerous specific details are set forth in order to provide a thorough understanding of the presented concepts. The presented concepts may be practiced without some or all of these specific details. In other instances, well known process operations have not been described in detail so as to not unnecessarily obscure the described concepts. While some concepts will be described in conjunction with the specific embodiments, it will be understood that these embodiments are not intended to be limiting.

Semiconductor fabrication often occurs within a semiconductor processing tool; such semiconductor processing tools may, in some implementations, have at least one processing chamber in which at least one process gas is flowed onto a semiconductor wafer. The semiconductor processing tool may have at least one panel forming a wall of the semiconductor processing tool. The semiconductor processing tool may also have at least one door through which access may be had to the inside of the semiconductor processing tool, which may include into the processing chamber.

An inspection window may be set within at least one wall panel or at least one door of the semiconductor processing tool so that at least a part of the semiconductor processing tool may be inspected or viewed without opening the door or removing the wall panel. Inspection and/or viewing of at least part of the semiconductor processing tool may be advantageous since it allows visual confirmation of various aspects of operations within the semiconductor processing tool, e.g., the proper placement of the wafer onto a pedestal may be verified.

The inspection window may be helpful to semiconductor processing because some semiconductor processing tools operate at a vacuum or near vacuum in the processing chamber and a window may allow for inspection and/or viewing of the semiconductor manufacturing process without disruption to the processing chamber environment. Other semiconductor processing tools may not operate under vacuum conditions but may, nonetheless, generally enclose the processing area to help prevent contaminants from entering the processing area—inspection windows may provide a mechanism by which operations within the processing tool may be inspected visually without opening the semiconductor processing tool. An inspection window may also be a safety enhancement to the semiconductor processing tool because some semiconductor processing tools use harmful process gases and/or chemicals during the semiconductor process and an inspection window may allow for inspection and/or viewing of the semiconductor processing tool without exposing a user to the harmful gases and/or chemicals, without requiring the user to utilize safety equipment, and/or without taking the time to remove the harmful gases and/or chemicals from the inside of the semiconductor processing tool.

Light from outside the semiconductor processing tool may pass through the inspection window and enter the inside of at least a part of the semiconductor processing tool, which may include the processing chamber. Light that enters the semiconductor processing tool and hits a wafer, including ambient light from, for example, the facility in which the semiconductor processing tool is housed and that contacts a wafer during an active semiconductor manufacturing process, may adversely affect the quality of the wafer. For example, one common semiconductor manufacturing process, photolithography, involves a light sensitive silicon wafer substrate that, in part, is exposed to UV light in order to form integrated circuits, and ambient light, for instance, from outside the semiconductor processing tool, may interfere with this photolithography process.

Without some obstruction between the light outside the semiconductor processing tool and inside at least part of the semiconductor processing tool, light may continually and/or repeatedly adversely affect the quality of at least one wafer inside the semiconductor processing tool.

One industry solution is to place an opaque window cover on the outside of the semiconductor processing tool which may prevent at least some of the light from passing through the inspection window into the semiconductor processing tool, which may include the processing chamber. The window cover may be hingedly connected to the door or the panel, may be secured to the door or the panel with a magnet, and/or may have a door knob with which to pull open the window cover in order to view inside a part of the semiconductor processing tool. The window cover may also be connected to the door or the panel through a variety of methods including magnets, screws, clamps, or brackets.

Having a window cover over the outside of the inspection window may prevent some light from entering the semiconductor processing tool, but the present inventors have determined that such a solution has several disadvantages. In a first example, the size and the configuration of some semiconductor processing tools, which may include the SABRE ANNEAL, or SABRE HTFE (High-Throughput Front End) and SABRE Core modules produced by Lam Research, may prevent the window cover from opening fully, and may therefore prevent full viewing and/or inspection through the inspection window. The door knob may also present a safety hazard in that it may catch or snag on clothing or equipment, or it may cause a puncture, abrasion, or impact hazard. In a second example in which the window cover is hingedly connected to the door or the panel and hinges open along a vertical axis that is along a side of the inspection window, similar to a conventional door, an open or partially open window cover may block at least a part of a second window nearby. In a third example, in which the window cover is hingedly connected to the door or the panel and hinges open along a horizontal axis that is above the inspection window, i.e. "flips up" to open, a user who opened the window may be required to hold open the window cover in order to look inside the semiconductor processing tool. A cover that "flips up" may require a user to support the cover in order to keep it open, which presents a safety hazard and ergonomic challenges to a tall user who may have to stoop while holding the window cover up in order to look through the inspection window, or it may present a challenge to a shorter user who may not be able to physically open and/or lift the window cover due to their height. A cover that "flips up" or "flips down" may present a safety hazard to a user, the door, the panel, and/or the window cover if the window cover is dropped or becomes unsecured and falls. Window covers may also protrude from the machine which, again, may present safety hazards.

Furthermore, if a window cover is moved and/or removed during an active semiconductor manufacturing process such that light may enter into a semiconductor processing chamber, then a wafer being processed could be ruined which could result in a product and/or financial loss. The present inventors have discovered that in some situations, in order to prevent this from occurring, the window cover may require an electrical interlock to prevent the window cover from being opened accidentally during such a process.

Another disadvantage of the window cover is that the window cover may become damaged or misshaped such that the window cover may not block all the light from entering the semiconductor processing tool through the window. A window cover that is not fully flush against the inspection window may also present a safety hazard to persons and equipment.

The present inventors have determined that inspection windows for semiconductor processing tools may be equipped with or modified to use smart films to allow for switchable inspection windows that may be used in place of the traditional window covering systems used today. The semiconductor processing tool smart window configurations discussed herein provide a new and safer mechanism for minimizing, reducing, or even eliminating the light that enters into the semiconductor processing tool through an inspection window.

The term "smart film," as used herein, refers to a layer of material that is configured to alternate between a transparent state and an opaque state in response to receipt of an electrical signal. Smart films may be made with different technologies; an example smart film may have at least two transparent conductive material layers contacting a liquid suspension layer or film that contains suspended particles that may change orientation in response to exposure to an electric current or voltage, thereby adjusting the amount of light that may pass through the suspended particles, while another example smart film may be made with at least two conductive layers contacting a polymer-dispersed liquid crystal layer. Some smart films may exist in an opaque state when no voltage is applied to the smart film and may then transition to a transparent state when a voltage is applied to the smart film; some other smart films may operate in the opposite manner. In some cases, smart films may incorporate a mechanically or electrically bistable mechanism for adjusting the amount of light transmissivity of the smart film and may remain in either the opaque or transparent state after being transitioned to that state by a control signal. Some smart films are able to block most visible light wavelengths, including some UV wavelengths. For example, testing has shown that smart films from Smart Tint, Inc., can block 95% or more of light in the 400 nm to 800 nm range. Some testing has also shown that some smart films are able to block 100% of the light wavelengths shorter than 550 nm, which some semiconductor wafer manufacturing processes may require. Some suitable smart films that may be used in practicing the concepts discussed below may, for example, be obtained from Sonte and Smart Tint, Inc. Some of these smart films may have an adhesive layer which may allow them to be adhered onto a surface.

FIG. 1 depicts an isometric exploded view of a first example semiconductor processing tool smart window kit for a semiconductor processing tool. As can be seen, the first example semiconductor processing tool smart window kit 100 is shown. The first example semiconductor processing tool smart window kit includes a smart film 102 that may be interposed between a first inspection window 104 and a first panel 106. The first inspection window 104 may be configured to be set into the first opening 108 which has a first boundary 110. As shown, the first opening 108 may be an opening in a portion of a semiconductor processing tool 112 (the majority of the tool is not shown in FIG. 1; only a rectangular portion of the tool is shown).

The smart film 102 may be placed adjacent to the first inspection window 104, and may be interposed between the first inspection window 104 and the first panel 106. In some embodiments, the smart film 102 may have an adhesive layer that may adhere it to the first inspection window 104 or to the first panel 106. The smart film 102 adhesive layer may be applied to the smart film by the manufacturer of the smart film 102 or by another person and/or machine.

In some embodiments of the semiconductor processing tool smart window kit 100 as shown in FIG. 1, the first panel 106 may be transparent, and it may be made from Lexan, a polymer, quartz, glass, or other transparent material that may be suitable for a semiconductor processing tool. The first panel 106 may protect the smart film 102 from damage which may be caused by users and/or the semiconductor manufacturing process. The first inspection window 104 may be transparent, and it may also be made from Lexan, a polymer, quartz, glass, or other transparent material suitable for a semiconductor processing tool.

The first example semiconductor processing tool smart window kit 100 may also have a mechanism for connecting the first panel 106 to the first inspection window. In some embodiments, the mechanism may include a series of first connecting holes 114 that extend through the first panel 106, extend through the first inspection window 104, and which may be aligned such that the first connecting holes 114 may permit a bolt, screw, or other connector to extend through the first connecting holes 114 and allow for securing the first panel 106 to the first inspection window 104. The first panel 106 may be connected to the first inspection window 104 through other mechanisms, such as a bolt and nut, adhesive, magnets, and/or clamps.

Some embodiments may also include the first inspection window 104 being connected to the semiconductor processing tool 112. The mechanism for such embodiments may include a nut and bolt combination configured to secure the window to the semiconductor processing tool. For instance, the nuts may be fastened to bolts which extend through the first connecting holes 114 (here, these holes extend through the wall of the semiconductor processing tool and through the first inspection window 104). In some embodiments, the mechanism that may connect the window to the semiconductor processing tool 112 may include other mechanical configurations and mechanisms that may include clamps, brackets, or magnets. The mechanisms that may connect the window to the semiconductor processing tool may also be configured to connect the first panel 106 to the first inspection window 104.

Other embodiments of semiconductor processing tool smart window kit may include the smart film 102 that is configured to be installed adjacent to the first inspection window 104, but may not include the first inspection window 104 (instead, the kit may modify or retrofit a pre-existing or pre-installed inspection window in the semiconductor processing tool) and/or may not include the first panel 106 (which may, in some cases, be omitted, although this may place the smart film 102 at an increased risk of damage).

Figure 2:
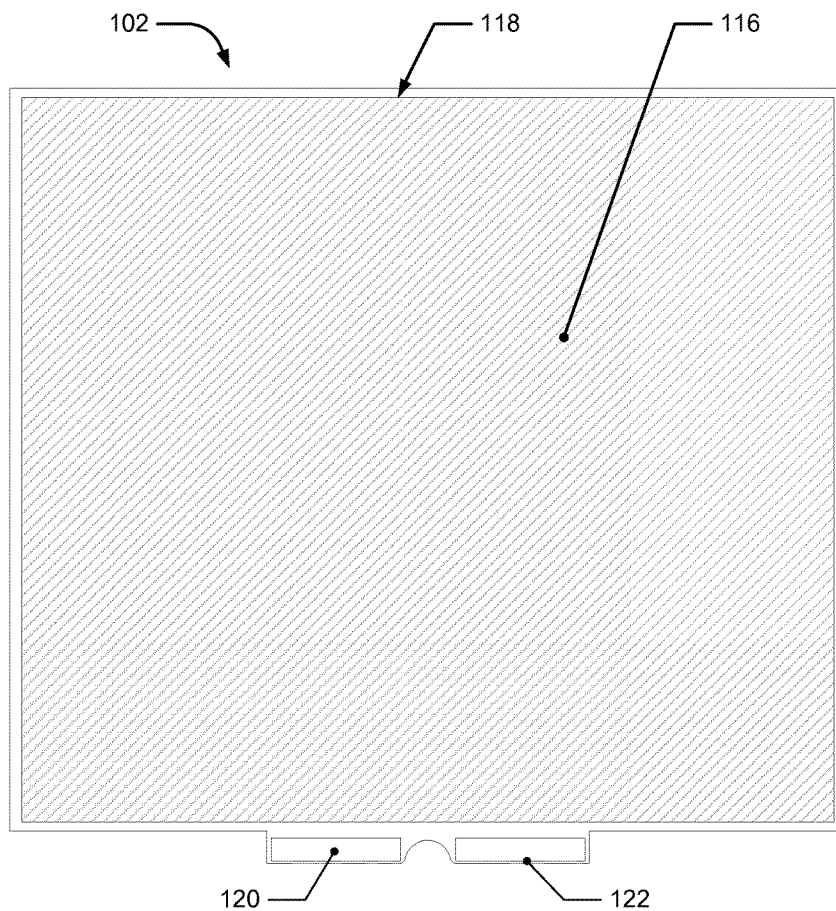
FIG. 2 depicts a plan view of a first example smart film of the first example semiconductor processing tool smart window kit of FIG. 1.

FIG. 2 depicts a plan view of the smart film 102 of the first example semiconductor processing tool smart window kit of FIG. 1. The smart film 102 includes an active area 116 (shown as crosshatched) that is defined by a second boundary 118, a first electrical contact pad 120, and a second electrical contact pad 122. The active area 116 is an area of the smart film 102 which is electronically controllable between an opaque state and a transparent state. In some embodiments the active area 116 may be configured to be opaque when no voltage is applied to it and to be transparent when a voltage is applied to it. In some embodiments the active area 116 may also be configured to be opaque when a voltage is applied to it and to be transparent when no voltage is applied to it. Some embodiments may have different transparent and/or opaque states. A first non-limiting example may have first opaque state that may be configured to block all visible light and a first transparent state that may be configured to be transparent to all visible light. A second non-limiting example may have an opaque state that blocks different wavelengths of light, which may include visible light, infrared, and ultraviolet, but allows some other wavelengths of light to pass through.

The second boundary 118 may be configured to be larger than the first boundary 110. In some embodiments the second boundary 118 may also be configured to be larger than the first boundary 110 such that when the active area 116 is in an opaque state, the active area 116 may not allow any light to enter the semiconductor processing tool, which may include the semiconductor processing chamber, through the first inspection window 104. The second boundary 118 may be of different sizes, configurations, and/or shapes which may include, but are not limited to, a square, rectangle, triangle, circle, a rectangle with rounded edges, or a square with rounded edges. For example, in some embodiments, the second boundary 118 may be equal to, or substantially equal to, the boundary of the smart film 102. In some embodiments, the active area 116 may not allow any light equal to and shorter than 550 nm wavelength to pass through the active area 116.

The first electrical contact pad 120 and the second electrical contact pad 122 may be configured to be electrically connected to the smart film 102 so that a voltage may be applied to the smart film 102 which may in turn change the active area 116 from an opaque state to a transparent state, or from a transparent state to an opaque state. In some embodiments the first electrical contact pad 120 and the second electrical contact pad 122 may be configured from a copper foil strip that may be placed on the smart film 102. The first electrical contact pad 120 and the second electrical contact pad 122 may also be placed in different areas on the smart film 102. The first electrical contact pad 120 and the second electrical contact pad 122 may be configured such that the first electrical contact pad 120 is "hot" and the second electrical contact pad 122 is "neutral", or vice versa. The first electrical contact pad 120 and the second electrical contact pad 122 may be configured into different sizes, configurations, and/or shapes.

In some example embodiments the smart film 102 may be configured so that it may be operable between a temperature at least as low as −10 degrees Celsius and as high as 60 degrees Celsius, it may be operable using an example voltage of 45+/−5 VAC, it may consume 0.05 Amps/m$^2$, it may consume 1 Watt/m$^2$, it may have a response time of at least less than 0.2 seconds, and/or it may have an operational lifetime of at least 80,000,000 cycles of transitioning between the opaque state and the transparent state.

Figure 3:
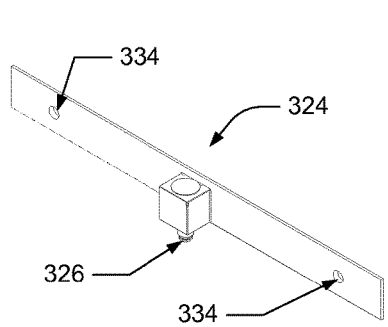
FIG. 3 depicts a first isometric view of an example electrical contact cover.
Figure 4:
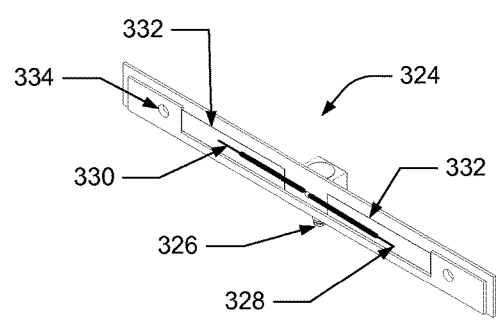
FIG. 4 depicts a second isometric view of the example electrical contact cover of FIG. 3.

FIG. 3 depicts a first isometric view of an example electrical contact cover. FIG. 4 depicts a second isometric view of the example electrical contact cover 324 of FIG. 3. The example electrical contact cover 324 may include a connector 326, a first electrical conductor 328, and a second electrical conductor 330. The first electrical conductor 328 may be configured to electrically connect with the first electrical contact pad 120; the second electrical conductor 330 may be configured to electrically connect with the second electrical contact pad 122. The first electrical conductor 328 and the second electrical conductor 330 may be connected with the connector 326, which may include an electrical termination into the connector 326.

In some embodiments the first electrical conductor 328 may be include, for example, a first insulated copper wire having the insulation removed at the end so as to expose a first part of the first copper wire such that it may be electrically connected to the first electrical contact pad 120. The second electrical conductor 330 may include, for example, a second insulated copper wire having the insulation removed at the end so as to expose a second part of the second copper wire such that it may be electrically connected to the second electrical contact pad 122. In some embodiments, the first electrical conductor 328 and the second electrical conductor 330 may be flat wire, may be configured to have a 600 VAC rating, and/or may be configured to withstand 6A at 30 degrees Celsius. The first electrical conductor 328 and the second electrical conductor 330 may both be contained within a third surrounding insulation. In some implementations, the first and second electrical conductors may be provided by a flat flex ribbon cable or flexible conductive traces, or by various other types of electrically conductive mechanisms.

In some embodiments the first electrical conductor 328 and the second electrical conductor 330 may be secured to the first electrical contact pad 120 and the second electrical contact pad 122, respectively, with a compression connection, which may be provided, for example, by an insulated adhesive tape 332. In some embodiments, other types of electrical connections may be used to electrically connect the electrical conductors of the electrical contact cover 324 and the smart film 102.

The connector 326 may be configured to be electrically connected to a power source. The connector 326 may be a branch connector and it may be configured to electrically connect with at least a second smart window within one or more semiconductor processing tools.

In some embodiments the electrical contact cover 324 may also be configured to be affixed to the first inspection window 104 or to the first panel 106. The electrical contact cover 324 may be configured to be affixed to the first inspection window 104 by an adhesive layer, clamps, brackets, or by a nut and bolt configuration which may use at least a second connecting hole 334 that may extend through the electrical contact cover 324 and through the first inspection window 104. The electrical contact cover 324 may be configured to be affixed to the first panel 106 by an adhesive layer, clamps, brackets, or by a nut and bolt configuration which may use at least a second connecting hole 334 that may extend through the electrical contact cover 324 and through the first panel 106.

Figure 5:
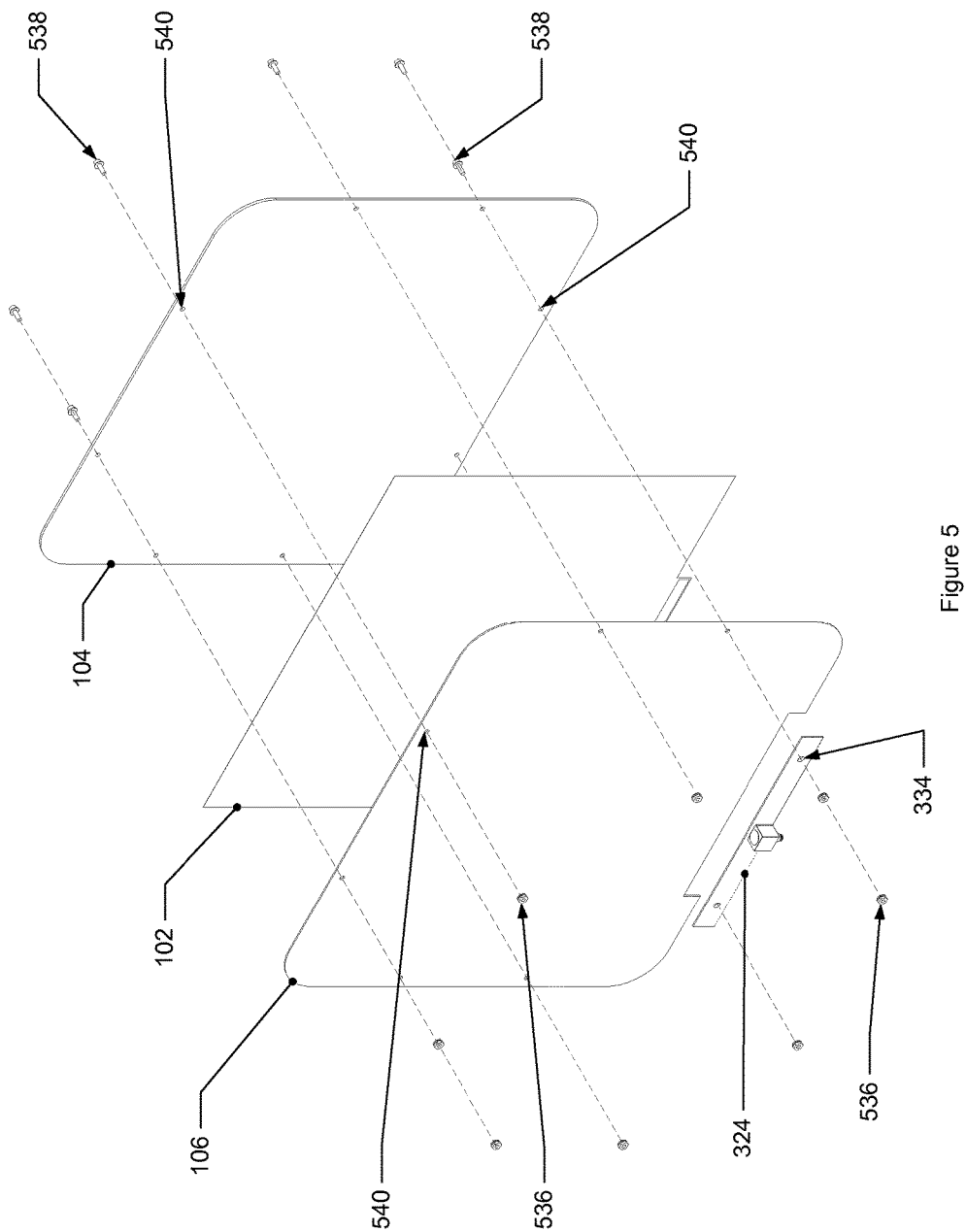
FIG. 5 depicts an isometric exploded view of a second example semiconductor processing tool smart window kit for a semiconductor processing tool.

FIG. 5 depicts an isometric exploded view of a second example semiconductor processing tool smart window kit for a semiconductor processing tool. The second example semiconductor processing tool smart window kit for a semiconductor processing tool may include the electrical contact cover 324, the first panel 106, the smart film 102, and the first inspection window 104. FIG. 5 also depicts example nuts 536 and bolts 538 for connecting the first panel 106 and the electrical contact cover 324 with the first inspection window 104 which may pass through a plurality of third connecting holes 540 that may extend through the first panel 106 and the first inspection window 104, and through the second connecting holes 334 that may extend through the electrical contact cover 324. The smart film 102 may be adhered to the first panel 106 or to the first inspection window 104. Some embodiments may not have the first panel 106.

The first inspection window 104 may be configured to be installed into a semiconductor processing tool. In some embodiments, the first inspection window 104 may be configured to be installed into a semiconductor processing tool through mechanisms which may include clamps, screws, or the nut 536 and bolt 538 mechanism for connecting the first panel 106 and the electrical contact cover 324 to the first inspection window 104 which may pass through the plurality of third connecting holes 540 that may extend through the first panel 106, the electrical contact cover 324, and the first inspection window 104.

The second example semiconductor processing tool smart window kit for a semiconductor processing tool may be configured with at least one or more of the embodiments of the semiconductor processing tool smart window kit described earlier herein, e.g., multiple smart films for multiple inspection windows may be included in a common smart window kit.

Figure 6:
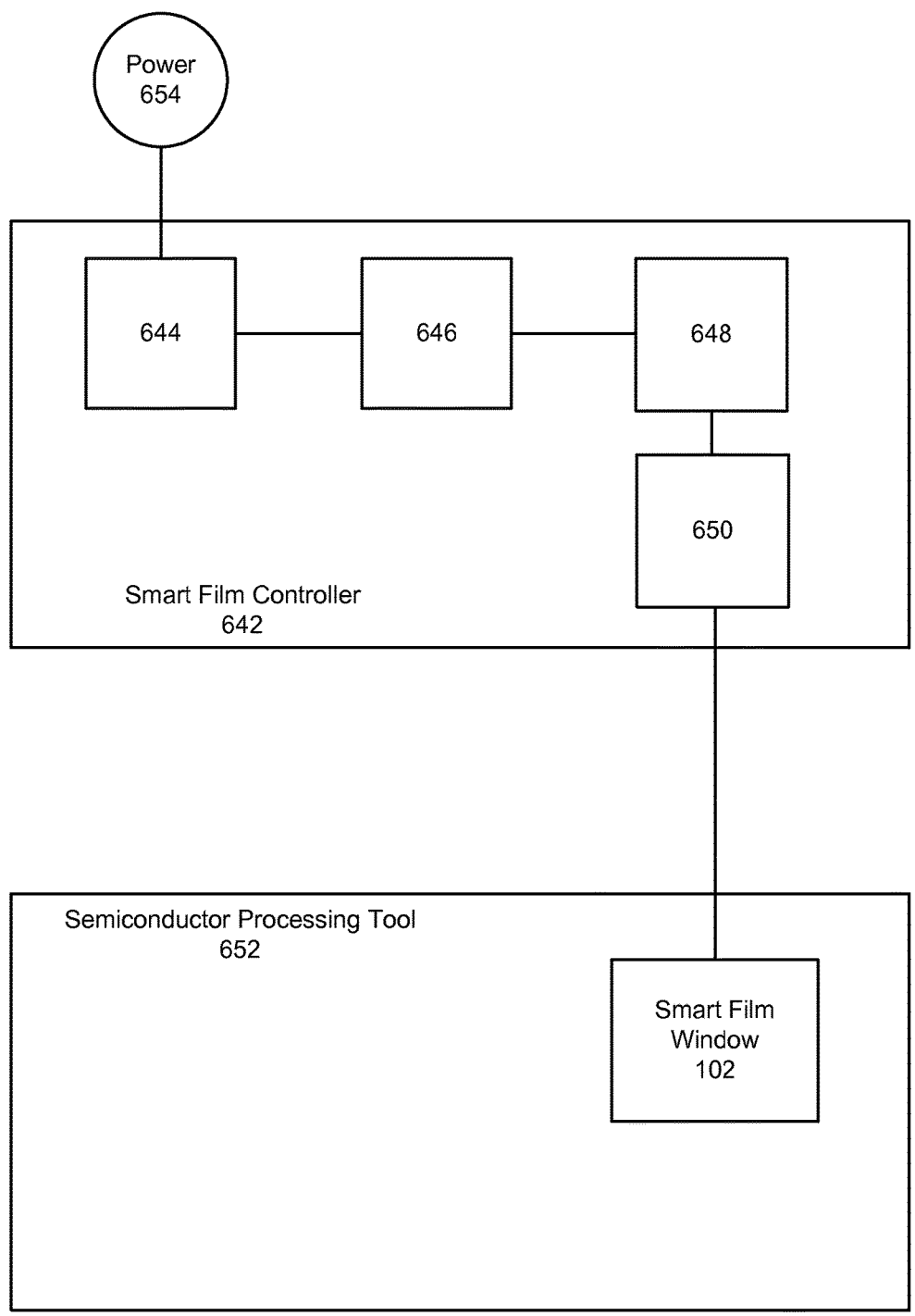
FIG. 6 depicts an example smart film controller for a semiconductor processing tool smart window kit for a semiconductor processing tool.

FIG. 6 depicts an example smart film controller 642 for a semiconductor processing tool smart window kit for a semiconductor processing tool. Such a controller may be used to control one or more smart film windows in the semiconductor processing tool, and may be included in a smart film kit in some embodiments. The example smart film controller 642 may include an input circuit breaker 644, a transformer 646, an output circuit breaker 648, and a smart film control switch 650. The smart film controller 642 may be employed to control the transparent state and the opaque state of the smart film 102 and/or more than one smart film 102 of a semiconductor processing tool 652. The input circuit breaker 644 may be configured to be electrically connected to a power source 654, which, in some embodiments, may include a power source 654 from the semiconductor processing tool 652. In other embodiments, the power source 654 may be a facility power source. The transformer 646 may be configured to be electrically connected to the power source 654 by way of the input circuit breaker 644 such that the input circuit breaker 644 may protect the transformer 646, for instance, from electrical surges or other electrical events. The input circuit breaker may, in some embodiments, also serve as a safety interlock—for example, if the smart films are of the variety where power must be applied to transition them to the transparent state, then the input circuit breaker may be turned off to prevent operation of the smart film control switches from changing the state of the smart films. In some embodiments, the transformer 646 may step down the voltage supplied from the power source 654. In some embodiments, the power source 654 may supply 120V AC power and the transformer 646 may step down the voltage to approximately 42V AC, which is one voltage at which some smart films operate. In some other embodiments, the transformer 646 may step up a voltage supplied from the power source 654 to match the operating voltage of the smart film in use.

The output circuit breaker 648 may be electrically connected to the transformer 646 and to the smart film control switch 650 and configured such that the output circuit breaker 648 may protect the smart film control switch 650, the smart film 102, and/or a user, for example, from a hazardous electrical event. The smart film control switch 650 may be electrically connected to the smart film 102 and configured to control the transparency state of smart film 102 between the transparent state and the opaque state.

In some implementations, the semiconductor processing tool 652 may include more than one smart film 102 and the smart film controller 642 may be configured to control one or more of the smart films 102. In some such implementations, all smart films 102 may be electrically connected to one single smart film control switch 650, which is electrically connected to one single output circuit breaker 648, which is connected to one single transformer 646. In some other implementations, each smart film 102 may have its own individual corresponding smart film control switch 650 and output circuit breaker 648, and all of the output circuit breakers 648 may be electrically connected to a single transformer 646. For example, if a semiconductor processing tool 652 has five smart films 102, then in some such embodiments, each one of the five smart films 102 would be electrically connected to its own smart film control switch 650, which would be electrically connected to its own output circuit breaker 648, and all five output circuit breakers 648 would be connected to one single transformer 646. In still some other embodiments, some smart films 102 may be electrically connected to one output circuit breaker and one smart film control switch, while some other smart films may be electrically connected to a second output circuit breaker and a second switch.

In some embodiments, the controller (or the functionality thereof) may be a processor-based controller, or may be part of a processor-based controller (such as a semiconductor processing tool controller). For example, a semiconductor processing tool may be controlled by one or more computers that are communicatively connected with various actuators, valves, sensors, relays, etc. and that control such components in order to carry out the steps of a semiconductor manufacturing process. Such a controller may include various input/output interfaces that allow the controller to control a piece of electronic equipment, such as a smart film, connected to one of the input/output interfaces. In such cases, the tool controller may have complete operational control over the smart film windows or may operate in parallel with a manually-activated system, such as the controller discussed above with reference to FIG. 6.

Figure 7:
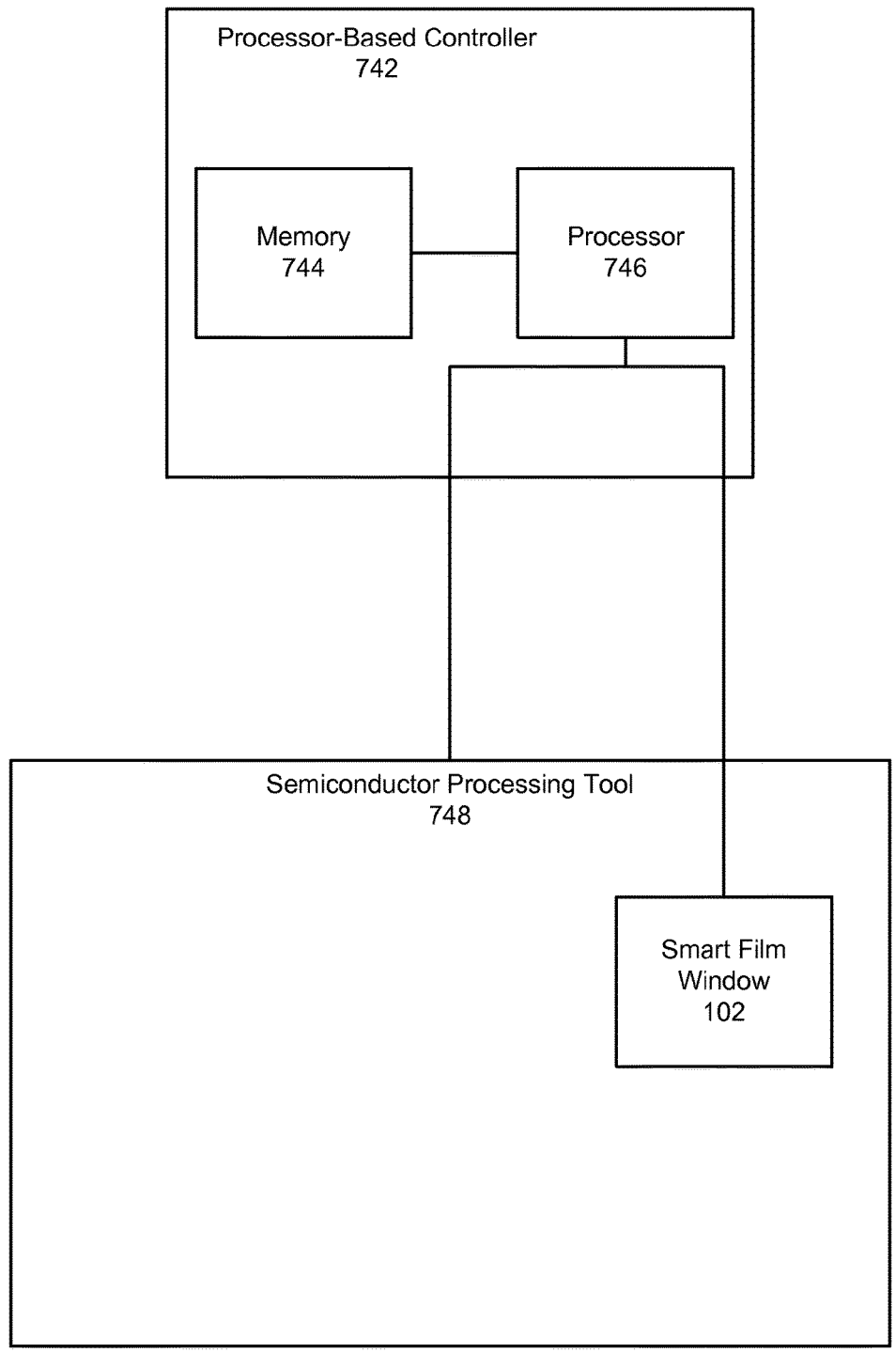
FIG. 7 depicts an example of a processor-based controller for a semiconductor processing tool smart window.

FIG. 7 depicts an example of a processor-based controller for a semiconductor processing tool smart window The processor-based controller 742 may include one or more memory devices 744 that may include one or more mass storage devices (not shown), and one or more processors 746. The processor 746 may include a CPU or computer, analog and/or digital input/output connections, etc. The memory may store computer-executable instructions for controlling the processor to perform various functions as described in more detail below. In some implementations, the processor-based controller 742 may be configured to control one or more smart films 102 on more than one semiconductor processing tool 748. As discussed above, in some implementations, the processor-based controller 742 may control all of the activities of the semiconductor processing tool 748. In other implementations, the processor-based controller 742 may be dedicated to only controlling smart films, or may be dedicated to controlling a subset of components of the semiconductor processing tool that includes one or more smart films. In such cases, the various functions and capabilities described below may be tailored to suit the level of control that the processor-based controller 742 has. For example, if the processor-based controller 742 is dedicated to only control smart film windows, then the functionality described below regarding control of valves, mass flow controllers, and other process equipment may be included in a different controller of the semiconductor processing tool.

The processor 746 of the processor-based controller 742 may execute system control software stored in and loaded into the memory 744. The system control software may include instructions for controlling the timing, mixture of gases, chamber and/or station pressure, chamber and/or station temperature, wafer temperature, target power levels, RF power levels, substrate pedestal, chuck and/or susceptor position, transparency of one or more smart films 102, and other parameters of a particular process performed by the semiconductor processing tool 748. The system control software may be configured in any suitable way. For example, various process tool component subroutines or control objects may be written to control operation of the process tool components necessary to carry out various process tool processes. System control software may be coded in any suitable computer readable programming language.

In some implementations, system control software may include input/output control (IOC) sequencing instructions for controlling the various parameters described above. In some implementations, there may be a user interface associated with the processor-based controller 742. The user interface may include a display screen, graphical software displays of the apparatus and/or process conditions, and user input devices such as pointing devices, keyboards, touch screens, microphones, etc.

Signals for monitoring the process and/or the smart film 102 may be provided by analog and/or digital communications to the processor-based controller 742 from various process tool sensors. The signals for controlling the process may be provided via analog and/or digital output connections of the semiconductor processing tool 748. Non-limiting examples of process tool sensors that may be monitored include mass flow controllers, pressure sensors (such as manometers), thermocouples, and/or a sensor configured to detect a transparency state of one or more smart films 102 (e.g., whether a smart film 102 is in a transparent state or opaque state), etc. Appropriately programmed feedback and control algorithms may be used with data from these sensors to maintain process conditions. For example, a sensor configured to detect whether a smart film 102 is in a transparent or opaque state may provide one or more signals to the controller, which is configured to receive, interpret, identify, analyze, and/or act in response to such signals, so that the controller may cause some action to occur if the smart film 102 is in the incorrect transparency state for a given semiconductor processing phase, e.g., change the smart film transparency to the correct state, send a notification to one or more users, sound an alarm, and/or store the signal in a memory. The processor-based controller 742 may provide program instructions for implementing various semiconductor fabrication processes. The program instructions may control a variety of process parameters, such as DC power level, RF bias power level, pressure, temperature, and the transparency state of one or more smart films 102, etc. As discussed earlier, in some implementations, the processor-based controller 742 may be a separate unit from a controller that controls the overall tool operation, e.g., in a retrofit kit, the semiconductor processing tool may already include a controller that is configured to control aspects of the semiconductor processing tool, and the smart film controller may be a separate unit that provides additional functionality needed to control the smart film(s). In such implementations, the processor-based controller 742 may also include one or more relays or other electrically-controllable switches that may be triggerable by the tool controller in order to cause the smart film windows to change state.

In some embodiments, the smart film 102 and/or the controller configured to control the transparency state of the smart film 102 may be configured to wirelessly connect to and/or be controlled by one or more remote devices. In some such configurations, the controller may be a smart film controller 642 or a processor-based controller 742, and the controller may be configured to communicate with a remote device via wireless interface. In some configurations, the controller may be configured to change the transparency state of the smart film based on instructions sent by a remote device. In some configurations, the controller may be configured to receive signals and/or instructions from the remote device, and in some other configurations the controller may be configured to both send and receive signals and/or instructions from the remote device. In some configurations, the signals sent to the remote device may indicate the transparency state of the smart film, e.g. whether the smart film is transparent or opaque. Some non-limiting examples of the wireless interfaces may include Bluetooth Base Rate/Enhanced Data Rate protocol, Bluetooth Low-Energy, or Wi-Fi. Some non-limiting examples of the remote device may include a remote control, computer, Wi-Fi router, mobile device, tablet, or cell phone. For a non-limiting example, the smart film may be electrically connected to the controller, the controller may be wirelessly connected to a smart phone via a Wi-Fi router, and the controller may be configured to receive signals from the smart phone which cause the controller to change the transparency state of the smart film.

In some embodiments, a semiconductor processing tool smart window kit may be configured to be installed on an existing first inspection window 104 of a semiconductor processing tool. Such embodiments may include the smart film 102 configured to be installed adjacent to the first inspection window 104 and configured to be adhered to the first inspection window 104. Such embodiments may also include the transparent first panel 106 which may be configured to be installed adjacent to the smart film 102, and affixed to the first inspection window 104 or to the semiconductor processing tool; the smart film 102 may be adhered to the first panel 106 or to the first inspection window 104. Such embodiments may also include the electrical contact cover 324 that may be configured to electrically connect to the smart film 102, and may be configured to be affixed to the first inspection window 104 and/or affixed to the first panel 106. Such embodiments may also include a smart film controller 642 or a processor-based controller 742. Such embodiments may also combine or remove attributes of the other embodiments described herein such that the semiconductor processing tool smart window kit may be configured to include some or all of the elements listed herein.

In some embodiments, a semiconductor processing tool smart window kit may be configured to replace a first inspection window 104 of a semiconductor processing tool. Such embodiments may include the smart film 102 installed adjacent to the first inspection window 104 and adhered to the first inspection window 104. Such embodiments may also include the transparent first panel 106 which may be installed adjacent to the smart film 102, and affixed to the first inspection window 104 or to the semiconductor processing tool; the smart film 102 may be adhered to the first panel 106 and/or to the first inspection window 104. Such embodiments may also include the electrical contact cover 324 that may be configured to electrically connect to the smart film 102, and may be configured to be affixed to the first inspection window 104 and/or affixed to the first panel 106. Such embodiments may also include the smart film controller 642 or a processor-based controller 742. Such embodiments may also combine or remove attributes of the other embodiments described herein such that the semiconductor processing tool smart window kit may be configured to include some or all of the elements listed herein.

Figure 8:
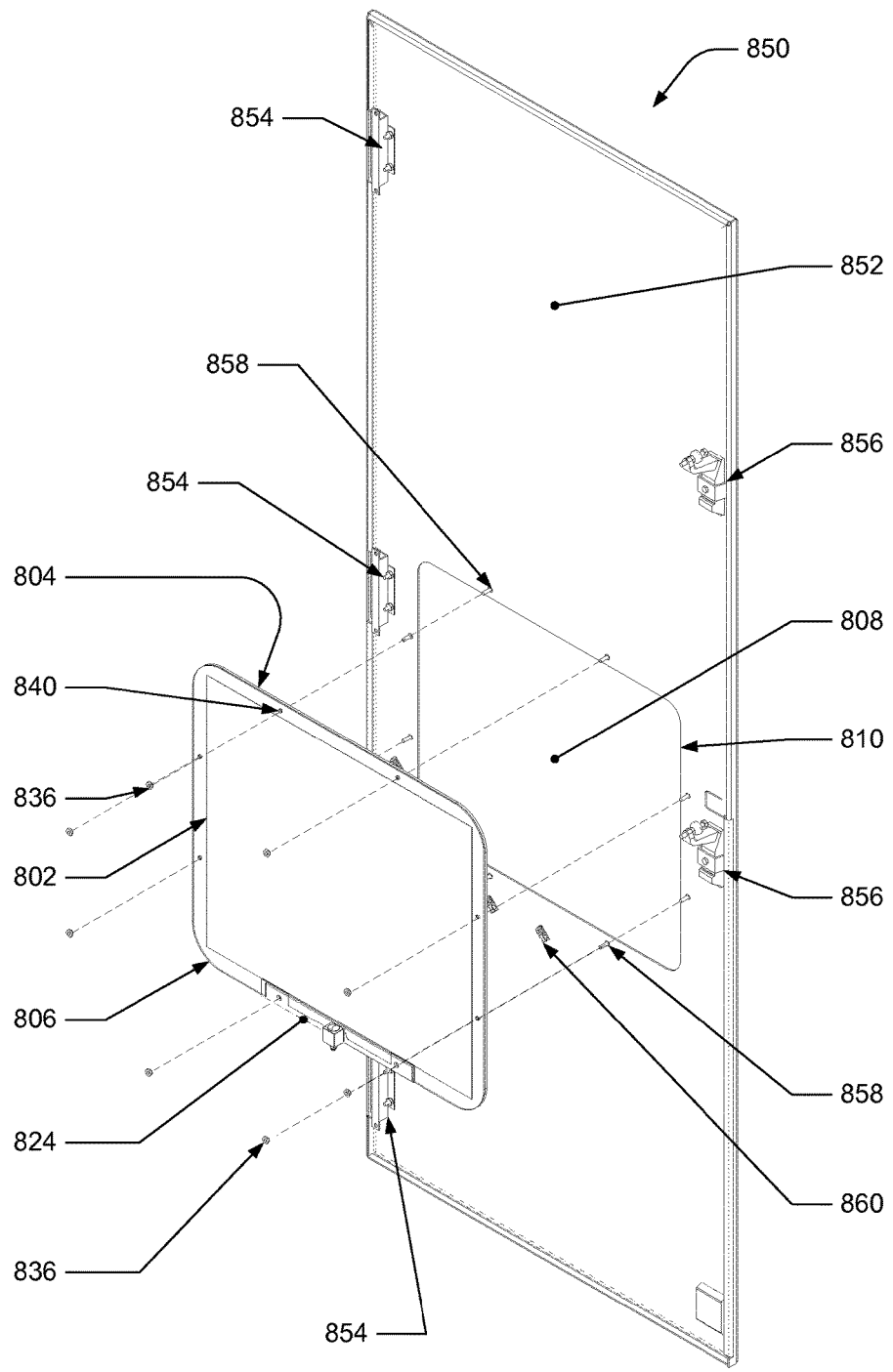
FIG. 8 depicts an isometric partially exploded view of a first example door for a semiconductor processing tool.

FIG. 8 depicts an isometric partially exploded view of a first example door 850 for a semiconductor processing tool. The first example door 850 includes a door panel 852, a first opening 808 with a first boundary 810, a smart film 802, a first inspection window 804, a first panel 806, an electrical contact cover 824, a hinge 854 (or some other mechanism specifically configured to connect the door 850 with the semiconductor processing tool), and a door latch 856. Some embodiments of the door 850 may include one or more, or a combination of some, of the embodiments and configurations of the semiconductor processing tool smart window kit herein described, including, but not limited to, elements of the smart film controller 642. In some embodiments of the door 850, the first opening 808 with the first boundary 810, the smart film 802, the first inspection window 804, the first panel 806, and/or the electrical contact cover 824 may include the embodiments and/or configurations of the first boundary 110, the smart film 102, the first inspection window 104, the first panel 106, and/or the electrical contact cover 824 herein described for the semiconductor processing tool smart window kit. Such embodiments may also combine or remove attributes of the other embodiments described herein.

By way of a first non-limiting example, one embodiment of the door 850 may include the smart film 802 interposed between the first inspection window 804 and the first panel 806 and placed adjacent to the first inspection window 804; the first inspection window 804 set into the first opening 808; the smart film 802 having an adhesive layer that may adhere it to the first inspection window 804 or to the first panel 806; and the electrical contact cover 824 connected to first inspection window 804. A second non-limiting example may include some of the elements of the first non-limiting example, except for the first panel 806.

Some embodiments of the first example door 850 for a semiconductor processing tool may have a mechanism for connecting the first panel 806, the first inspection window 804, and/or the electrical contact cover 824 to the door panel 852. Some embodiments and/or configurations of such mechanism may include the embodiments described herein for the semiconductor processing tool smart window kit.

In some embodiments, the mechanism may include a series of fourth connecting holes 840 that extend through the first panel 806, extend through the first inspection window 804, and/or through the first electrical contact cover 824; and which may be aligned such that the fourth connecting holes 840 may permit a stud 858, screw, or other connector to extend through the fourth connecting holes 840 and secure the first panel 806, the first inspection window 804, and/or the first electrical contact cover 824 to the door panel 852 with a nut 836 or other connector. The stud 858 may be affixed to the door panel 852 or may extend through the fourth connecting holes 840 that may extend through the door panel 852.

In some embodiments, the door panel 852 may also include a mechanism for securing wiring, which may include one or more cable holders 860 that may be configured to hold one or more wires and/or conduit.

The mechanical mechanism, e.g., hinge 854 and door latch 856, of the door 850 may be configured to operably connect the door panel 852 to the semiconductor processing tool. The mechanical mechanism 854 may be configured to allow the door 850 to open and close, or to be removed entirely. In some embodiments, the mechanical mechanism 854 may include, in some embodiments, at least a hinge, at least a latch, and/or at least a clamp. In FIG. 8, the mechanical mechanism includes more than one hinge 854 and more than one latch 856.

In some embodiments, the door 850 may be configured to be installed on a new semiconductor processing tool, in which such embodiments may be configured to include some or all of the elements and/or configurations of the door 850 described herein. In some embodiments, the door 850 may be configured to replace an existing door on a semiconductor processing tool, in which such embodiments may be configured to include some or all of the elements and/or configurations of the door 850 described herein.

Figure 9:
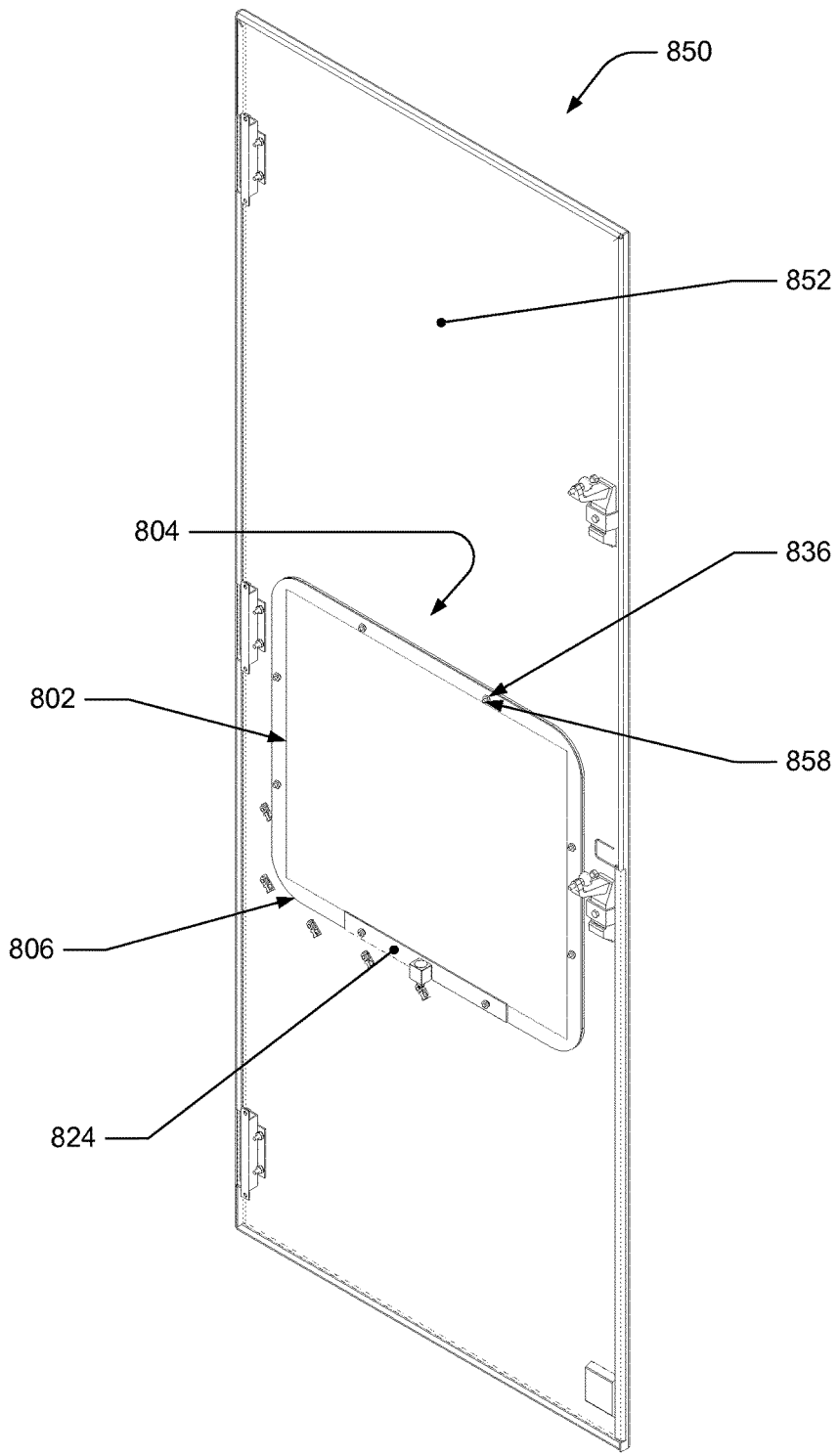
FIG. 9 depicts an isometric view of the first example door for a semiconductor processing tool of FIG. 8.

FIG. 9 depicts an isometric view of the first example door 850 for a semiconductor processing tool of FIG. 8. In this figure, the first inspection window 804 may be set within the first opening 808, the smart film 802 is interposed adjacent to the first inspection window 804, the first panel 806 may be adjacent to the smart film 802, and the smart film 802 may be adhered to the first inspection window 804 or to the first panel 806. The first inspection window 804 and the smart film 802 may also be affixed to the door panel 852 by a the fourth connecting holes 840 that extend through the first panel 806 and the first inspection window 804, and which may be aligned such that the fourth connecting holes 840 may permit a stud 858 to extend through the fourth connecting holes 840 and secure the first panel 806 and the first inspection window 804 to the door panel 852 with a nut 836. The stud 858 may be affixed to the door panel 852 or may extend through the fourth connecting holes 840 that extend through the door panel 852. The electrical contact cover 824 may also be affixed to the first inspection window 804 by a mechanism that may include a series of fourth connecting holes 840 that extend through the electrical contact cover 824, through the first inspection window 804, and which may be aligned such that the fourth connecting holes 840 may permit a stud 858 to extend through the fourth connecting holes 840 and secure the electrical contact cover 824 to the first inspection window 804 and/or to the door panel 852 with a nut 836. The stud 858 may be affixed to the door panel 852 or may extend through the fourth connecting holes 840 that extend through the door panel 852.

Figure 10:
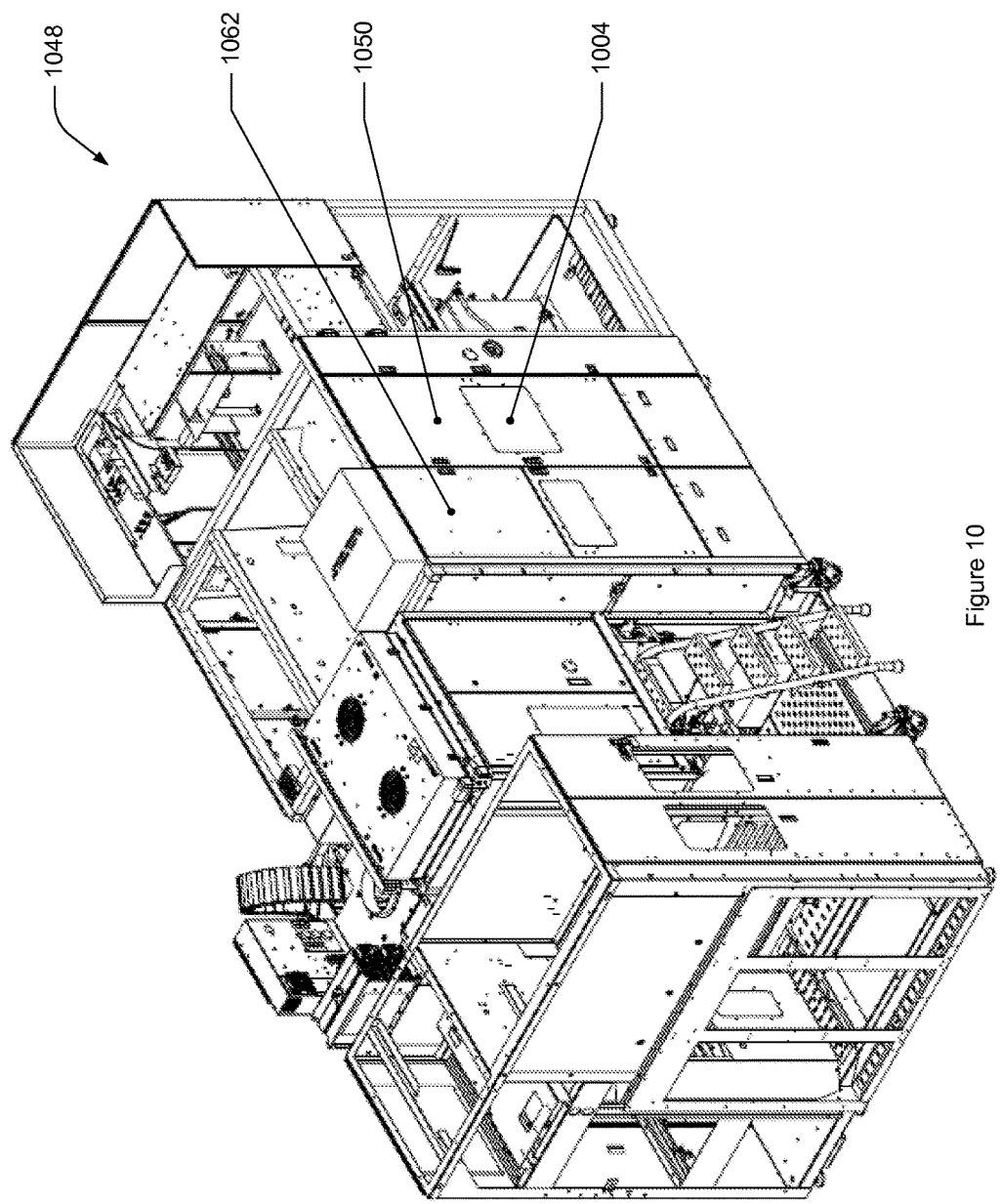
FIG. 10 depicts an isometric view of a first example semiconductor processing tool.

FIG. 10 depicts an isometric view of a first example semiconductor processing tool. The semiconductor processing tool 1048 may include at least one door 1050 and/or at least one first inspection window 1004. In some embodiments, the at least one door 1050 may include one or more embodiments and/or configurations of the door 850 previously described herein. In some embodiments, the semiconductor processing tool 1048 may include at least one door without an inspection window 1062. Some such embodiments may be configured to have a first inspection window and may include one or more embodiments and/or configurations of the door and/or semiconductor processing tool smart window kit as herein described. In some embodiments, the first inspection window 1004 may be configured to have one or more of the embodiments of the semiconductor processing tool smart window kit herein described. The semiconductor processing tool may also include the controller that may include one or more embodiments and/or configurations as previously described herein.

In some embodiments of the semiconductor processing tool, the semiconductor processing tool smart window kit and/or the door for a semiconductor processing tool may be configured to be placed on and in other aspects of the semiconductor processing tool, which may include a part of a processing chamber. For a non-limiting example, the semiconductor processing tool smart window kit may be configured to be placed on a circular inspection window of a processing chamber within the semiconductor processing tool.

Figure 11:
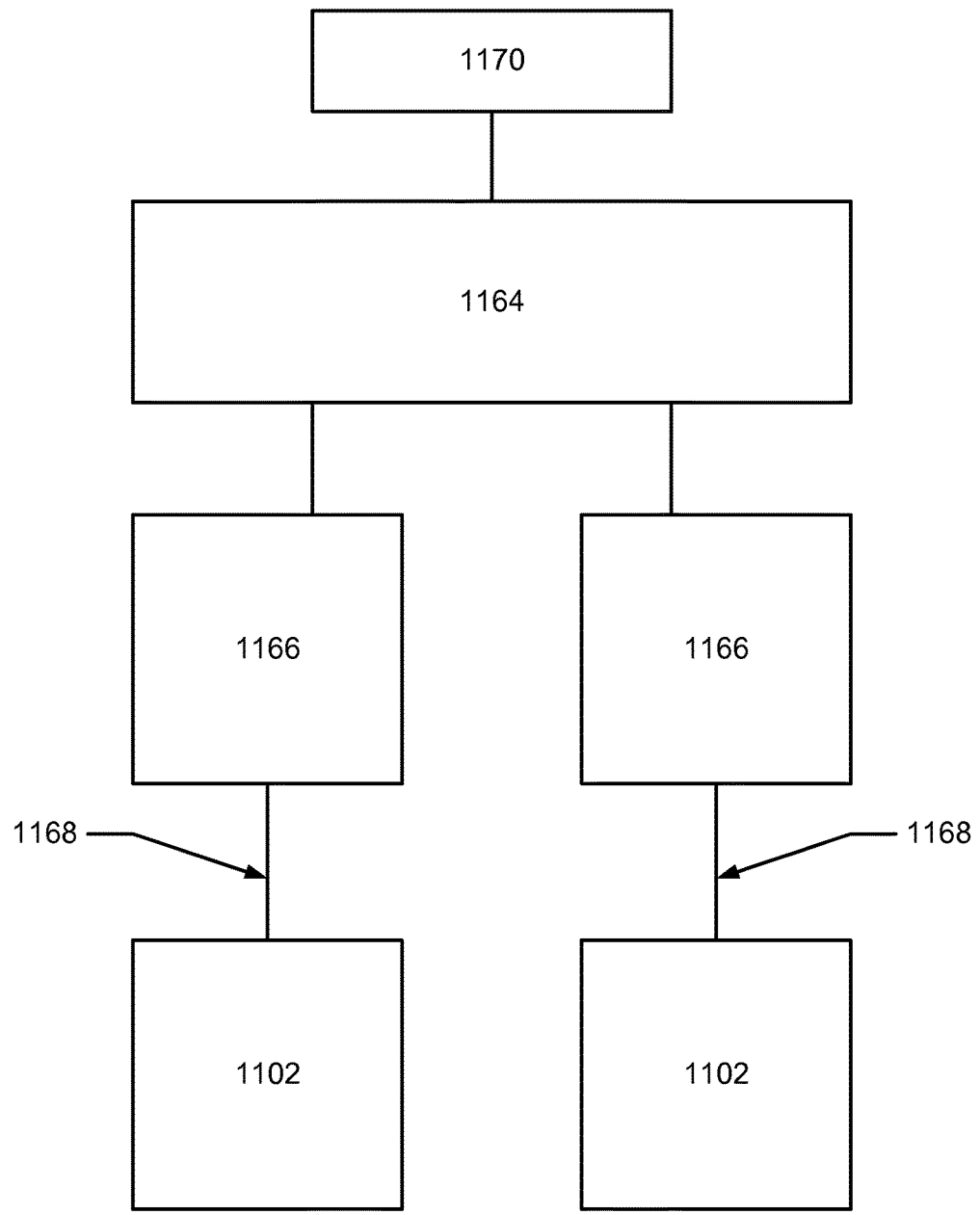
FIG. 11 depicts an example configuration of a lockout for a second example semiconductor processing tool.

In some embodiments, a lockout mechanism may be included with the smart film kit for a semiconductor processing tool. Such a lockout mechanism may be configured to prevent unintentional activations or deactivations of the smart films. FIG. 11 depicts an example configuration of a lockout for a second example semiconductor processing tool. The example configuration of a lockout for a second example semiconductor processing tool may include a lockout 1164, and one or more switches 1166, electrical connections 1168, and smart films 1102. Each switch 1166 may be electrically connected in line with one of the smart films 1102 and the power source 1170, and configured to electrically break the connection between the smart film 1102 and the power source and/or electrically connect the smart film 1102 with the power source, thereby causing the corresponding smart film 1102 to transition between the opaque state and the transparent state. In this non-limiting example, the smart film 1102 is configured to turn transparent when a voltage is applied, but some other embodiments of the lockout mechanism may be configured to provide similar lockout functionality for a smart film that may operate in the opposite manner, e.g., turn opaque when a voltage is applied. In some example embodiments, the lockout 1164 may be a timer switch that automatically engages after some period of time has elapsed since it was last disengaged (or vice versa), e.g., one minute, five minutes, etc. Thus, in order to transition a smart film 1102 from the opaque state to the transparent state, the user must disengage the lockout 1164 and actuate the switch 1166 for that smart film 1102. Even if the user then forgets to return the smart film to its opaque state using the switch 1166, the lockout 1164 may automatically break the circuit (or otherwise "override" the switch 1166) when the timer has expired, causing the smart film 1102 to revert to the opaque state. If multiple smart films 1102 are all connected to the same lockout 1164, then the lockout 1164 may cause all of these smart films 1102 to operate in this manner.

The lockout 1164 may also or alternatively be configured to prevent the switch 1166 from causing the smart film 1102 to transition into the transparent state during a phase of semiconductor processing when the smart film is associated with being in an opaque state. In some embodiments, it may be desired that at least one wafer being processed during at least one semiconductor processing is not exposed to light, for which the lockout 1164 may be configured to prevent the switch 1166 from transitioning the smart film 1102 to the transparent state during this at least one semiconductor processing phase. The application of a lockout to a particular semiconductor processing phase, and/or the lockout's configuration for the semiconductor processing phase and/or tool, may be configured to the semiconductor processing tool through manual input, mechanical input, electrical mechanism, a timer, and/or one or more programs stored in a controller for the semiconductor processing tool. In some embodiments, for example, one lockout may be affixed to the semiconductor processing tool and configured to prevent all the smart films of the semiconductor processing tool from being switched to the transparent state during every semiconductor processing phase. In other embodiments, one lockout 1164 may apply to more than one smart film 1102 in a semiconductor processing tool, and/or more than one smart film in more than one a semiconductor processing tool.

It is also to be understood that the functionality of the lockout 1164 may alternatively be provided via computer-executable instructions executed by a controller. For example, a controller for a semiconductor processing tool may be configured to engage lockout functionality, e.g., not permit the smart films to be transitioned from opaque to transparent, during any time periods when certain designated photo-sensitive semiconductor processing operations are being performed. Alternatively, the controller may, during such time periods, allow the smart films to be transitioned to the transparent state responsive to an operator request (such as the operator pushing a button that ordinarily causes the smart film to change state), but may only allow the smart films to be transitioned to such a state for a limited duration of time, e.g., 5 seconds or 10 seconds.

Unless the context of this disclosure clearly requires otherwise, throughout the description and the claims, the words "comprise," "comprising," and the like are to be construed in an inclusive sense as opposed to an exclusive or exhaustive sense; that is to say, in a sense of "including, but not limited to." Words using the singular or plural number also generally include the plural or singular number respectively. Additionally, the words "herein," "hereunder," "above," "below," and words of similar import refer to this application as a whole and not to any particular portions of this application. When the word "or" is used in reference to a list of two or more items, that word covers all of the following interpretations of the word: any of the items in the list, all of the items in the list, and any combination of the items in the list. The term "implementation" refers to implementations of techniques and methods described herein, as well as to physical objects that embody the structures and/or incorporate the techniques and/or methods described herein.

There are many concepts and implementations described and illustrated herein. While certain features, attributes and advantages of the implementations discussed herein have been described and illustrated, it should be understood that many others, as well as different and/or similar implementations, features, attributes and advantages of the present inventions, are apparent from the description and illustrations. As such, the above implementations are merely exemplary. They are not intended to be exhaustive or to limit the disclosure to the precise forms, techniques, materials and/or configurations disclosed. Many modifications and variations are possible in light of this disclosure. It is to be understood that other implementations may be utilized and operational changes may be made without departing from the scope of the present disclosure. As such, the scope of the disclosure is not limited solely to the description above because the description of the above implementations has been presented for the purposes of illustration and description.

Importantly, the present disclosure is neither limited to any single aspect nor implementation, nor to any single combination and/or permutation of such aspects and/or implementations. Moreover, each of the aspects of the present disclosure, and/or implementations thereof, may be employed alone or in combination with one or more of the other aspects and/or implementations thereof. For the sake of brevity, many of those permutations and combinations will not be discussed and/or illustrated separately herein.

What is claimed is:

1. A semiconductor processing tool smart window kit for a semiconductor processing tool that has at least one first inspection window set in a first opening, the first opening defined by a first boundary and the semiconductor processing tool smart window kit comprising:
   a smart film, the smart film comprising:
      a first electrical contact pad, and
      a second electrical contact pad; and
   an electrical contact cover, the electrical contact cover comprising:
      a first electrical conductor,
      a second electrical conductor, and
      a connector, wherein:
         the smart film has an active area that is electronically controllable between a transparent state and an opaque state,
         the active area is defined by a second boundary,
         the second boundary is sized larger than the first boundary,
         the smart film is configured to be installed adjacent to the first inspection window,
         the first electrical conductor is electrically connected to the first electrical contact pad,
         the second electrical conductor is electrically connected to the second electrical contact pad, and the first electrical conductor and the second electrical conductor are connected with the connector.

2. The semiconductor processing tool smart window kit of claim 1, further comprising a first inspection window wherein the smart film has an adhesive backing configured to allow the smart film to be adhered to the first inspection window.

3. The semiconductor processing tool smart window kit of claim 2, further comprising a first panel, wherein:
the first panel is transparent,
the smart film is configured to be interposed between the first inspection window and the first panel, and
the smart film is configured to be adhered to an item selected from the group consisting of the first panel and the first inspection window.

4. The semiconductor processing tool smart window kit of claim 1, further comprising a first panel, wherein:
the first panel is transparent,
the smart film is configured to be interposed between the first inspection window and the first panel, and
the smart film is configured to be adhered to an item selected from the group consisting of the first panel and the first inspection window.

5. The semiconductor processing tool smart window kit of claim 1, wherein the electrical contact cover is configured to be affixed to the first inspection window.

6. The semiconductor processing tool smart window kit of claim 1, further comprising a first panel, wherein:
the first panel is transparent;
the smart film is configured to be interposed between the first inspection window and the first panel;
the smart film is configured to be adhered to an item selected from the group consisting of the first panel and the first inspection window; and
the electrical contact cover is configured to be affixed to an item selected from the group consisting of the first inspection window and the first panel.

7. The semiconductor processing tool smart window kit of claim 1, further comprising a smart film controller having:
a transformer;
at least one circuit breaker; and
at least one smart film control switch, wherein:
the at least one circuit breaker and the transformer are configured to be electrically connected to a power source,
the at least one circuit breaker and the transformer are electrically connected to the at least one smart film control switch,
the at least one smart film control switch is electrically connected to at least one smart film, and
the at least one smart film control switch is configured to cause the at least one smart film to transition between the transparent state and the opaque state when actuated and when the at least one circuit breaker and the transformer are electrically connected to the power source.

8. The semiconductor processing tool smart window kit of claim 1, further comprising:
a switch, and
a lockout, wherein:
the switch is electrically connected to the smart film,
the switch is configured to cause the smart film to transition between the transparent state and the opaque state, and
the lockout is configured to prevent the switch from causing the smart film to transition into the transparent state during a phase of semiconductor processing when the smart film is associated with being in an opaque state.

9. A door for a semiconductor processing tool, the door comprising:
a door panel;
mechanical features to operably connect the door panel to the semiconductor processing tool;
a first inspection window set in a first opening in the door panel;
a smart film, the smart film comprising:
a first electrical contact pad, and
a second electrical contact pad; and
an electrical contact cover, the electrical contact cover comprising:
a first electrical conductor,
a second electrical conductor, and
a connector, wherein:
the first opening is defined by a first boundary,
the smart film has an active area that is electronically controllable between a transparent state and an opaque state,
the active area is defined by a second boundary,
the second boundary is sized larger than the first boundary,
the smart film is configured to be installed adjacent to the first inspection window,
the first electrical conductor is electrically connected to the first electrical contact pad,
the second electrical conductor is electrically connected to the second electrical contact pad, and
the first electrical conductor and the second electrical conductor are electrically connected with the connector.

10. The door of claim 9, wherein the smart film is adhered to the first inspection window with an adhesive layer.

11. The door of claim 9, further comprising a first panel, wherein:
the first panel is transparent,
the smart film is interposed between the first inspection window and the first panel, and
the smart film is adhered with an adhesive layer to an item selected from the group consisting of the first panel and the first inspection window.

12. The door of claim 9, wherein the electrical contact cover is configured to be affixed to the first inspection window.

13. The door of claim 9, further comprising a first panel, wherein:
the first panel is transparent,
the smart film is interposed between the first inspection window and the first panel,
the smart film is adhered to an item selected from the group consisting of the first panel and the first inspection window, and
the electrical contact cover is configured to be affixed to an item selected from the group consisting of the first inspection window and the first panel.

14. The door of claim 9, further comprising a smart film controller having:
a transformer;
at least one circuit breaker; and
at least one smart film control switch, wherein:
the at least one circuit breaker and the transformer are configured to be electrically connected to a power source, the at least one circuit breaker and the transformer are electrically connected to the at least one smart film control switch,
the at least one smart film control switch is electrically connected to at least one smart film, and
the at least one smart film control switch is configured to cause the at least one smart film to transition between the transparent state and the opaque state when actuated and when the at least one circuit breaker and the transformer are electrically connected to the power source.

15. The door of claim 9, further comprising:
a switch, and
a lockout, wherein:
the switch is electrically connected to the smart film,
the switch is configured to cause the smart film to transition between the transparent state and the opaque state, and
the lockout is configured to prevent the switch from causing the smart film to transition into the transparent state during a phase of semiconductor processing when the smart film is associated with being in an opaque state.

16. A semiconductor processing tool, the semiconductor processing tool comprising:
a first inspection window set in a first opening in the semiconductor processing tool;
a smart film, the smart film comprising:
a first electrical contact pad, and
a second electrical contact pad; and
an electrical contact cover, the electrical contact cover comprising:
a first electrical conductor,
a second electrical conductor, and
a connector, wherein:
the first opening is defined by a first boundary,
the smart film has an active area that is electronically controllable between a transparent state and an opaque state,
the active area is defined by a second boundary,
the second boundary is sized larger than the first boundary,
the smart film is configured to be installed adjacent to the first inspection window,
the first electrical conductor is electrically connected to the first electrical contact pad,
the second electrical conductor is electrically connected to the second electrical contact pad, and
the first electrical conductor and the second electrical conductor are connected to the connector.

17. The semiconductor processing tool of claim 16, wherein the smart film is adhered to the first inspection window with an adhesive layer.

18. The semiconductor processing tool of claim 16, further comprising a first panel, wherein:
the first panel is transparent,
the smart film is interposed between the first inspection window and the first panel, and
the smart film is adhered with an adhesive layer to an item selected from the group consisting of the first panel and the first inspection window.

19. The semiconductor processing tool of claim 16, wherein the electrical contact cover is configured to be affixed to the first inspection window.

20. The semiconductor processing tool of claim 16, further comprising a first panel, wherein:
the first panel is transparent,
the smart film is interposed between the first inspection window and the first panel,
the smart film is adhered to an item selected from the group consisting of the first panel and the first inspection window, and
the electrical contact cover is configured to be adhered to an item selected from the group consisting of the first inspection window and the first panel.

21. The semiconductor processing tool of claim 16, further comprising a smart film controller having:
a transformer;
at least one circuit breaker; and
at least one smart film control switch, wherein:
the at least one circuit breaker and the transformer are configured to be electrically connected to a power source,
the at least one circuit breaker and the transformer are electrically connected to the at least one smart film control switch,
the at least one smart film control switch is electrically connected to at least one smart film, and
the at least one smart film control switch is configured to cause the at least one smart film to transition between the transparent state and the opaque state when actuated and when the at least one circuit breaker and the transformer are electrically connected to the power source.

22. The semiconductor processing tool of claim 16, further comprising:
a semiconductor processing controller having:
at least one memory; and
at least one processor communicatively connected with the memory and configured to be communicatively connected with the smart film and the semiconductor processing tool, wherein the at least one memory stores computer-executable instructions for controlling the at least one processor to:
receive a signal from the semiconductor processing tool that indicates that the semiconductor processing tool is engaged in performing a first semiconductor manufacturing process on a semiconductor wafer; and
cause, in response to receiving the signal and when the smart film is in the transparent state, the smart film to enter the opaque state.

23. The semiconductor processing tool of claim 16, further comprising:
a switch, and
a lockout, wherein:
the switch is electrically connected to the smart film,
the switch is configured to cause the smart film to transition between the transparent state and the opaque state, and
the lockout is configured to prevent the switch from causing the smart film to transition into the transparent state during a phase of semiconductor processing when the smart film is associated with being in an opaque state.

24. A semiconductor processing tool smart window kit for a semiconductor processing tool that has at least one first inspection window set in a first opening, the first opening defined by a first boundary and the semiconductor processing tool smart window kit comprising:
a smart film;
a transformer;
at least one circuit breaker; and
at least one smart film control switch, wherein:

the smart film has an active area that is electronically controllable between a transparent state and an opaque state, the active area is defined by a second boundary, the second boundary is sized larger than the first boundary, the smart film is configured to be installed adjacent to the first inspection window, the at least one circuit breaker and the transformer are configured to be electrically connected to a power source, the at least one circuit breaker and the transformer are electrically connected to the at least one smart film control switch, the at least one smart film control switch is electrically connected to at least one smart film, and the at least one smart film control switch is configured to cause the at least one smart film to transition between the transparent state and the opaque state when actuated and when the at least one circuit breaker and the transformer are electrically connected to the power source.

25. A door for a semiconductor processing tool, the door comprising:
- a door panel;
- mechanical features to operably connect the door panel to the semiconductor processing tool;
- a first inspection window set in a first opening in the door panel;
- a smart film;
- a transformer;
- at least one circuit breaker; and
- at least one smart film control switch, wherein:
  - the first opening is defined by a first boundary,
  - the smart film has an active area that is electronically controllable between a transparent state and an opaque state,
  - the active area is defined by a second boundary,
  - the second boundary is sized larger than the first boundary,
  - the smart film is configured to be installed adjacent to the first inspection window,
  - the at least one circuit breaker and the transformer are configured to be electrically connected to a power source,
  - the at least one circuit breaker and the transformer are electrically connected to the at least one smart film control switch,
  - the at least one smart film control switch is electrically connected to at least one smart film, and
  - the at least one smart film control switch is configured to cause the at least one smart film to transition between the transparent state and the opaque state when actuated and when the at least one circuit breaker and the transformer are electrically connected to the power source.

26. A semiconductor processing tool, the semiconductor processing tool comprising:
- a first inspection window set in a first opening in the semiconductor processing tool;
- a smart film;
- a switch; and
- a lockout, wherein:
  - the first opening is defined by a first boundary,
  - the smart film has an active area that is electronically controllable between a transparent state and an opaque state,
  - the active area is defined by a second boundary,
  - the second boundary is sized larger than the first boundary,
  - the smart film is configured to be installed adjacent to the first inspection window,
  - the switch is electrically connected to the smart film,
  - the switch is configured to cause the smart film to transition between the transparent state and the opaque state, and
  - the lockout is configured to prevent the switch from causing the smart film to transition into the transparent state during a phase of semiconductor processing when the smart film is associated with being in an opaque state.

27. A semiconductor processing tool, the semiconductor processing tool comprising:
- a first inspection window set in a first opening in the semiconductor processing tool;
- a smart film; and
- a semiconductor processing controller having:
  - at least one memory; and
  - at least one processor communicatively connected with the memory and configured to be communicatively connected with the smart film and the semiconductor processing tool, wherein:
  - the first opening is defined by a first boundary,
  - the smart film has an active area that is electronically controllable between a transparent state and an opaque state,
  - the active area is defined by a second boundary,
  - the second boundary is sized larger than the first boundary,
  - the smart film is configured to be installed adjacent to the first inspection window, and
  - the at least one memory stores computer-executable instructions for controlling the at least one processor to:
    - receive a signal from the semiconductor processing tool that indicates that the semiconductor processing tool is engaged in performing a first semiconductor manufacturing process on a semiconductor wafer; and
    - cause, in response to receiving the signal and when the smart film is in the transparent state, the smart film to enter the opaque state.

* * * * *